United States Patent [19]

Seem

[11] Patent Number: 5,523,086

[45] Date of Patent: Jun. 4, 1996

[54] METHOD FOR MANUFACTURING A HEALTH FOOD UTILIZING A GARLIC

[76] Inventor: Hui-Sub Seem, 319-70, Jungbang-Dong, KeongSan, Keongbuk, Rep. of Korea

[21] Appl. No.: 366,504

[22] Filed: Dec. 30, 1994

[51] Int. Cl.⁶ ..................................................... A61K 35/78
[52] U.S. Cl. ...................... 424/195.1; 426/425; 426/431; 426/541; 426/542; 426/655; 426/658
[58] Field of Search .................... 424/195.1; 426/431, 426/541, 542, 655, 658, 425

[56] References Cited

U.S. PATENT DOCUMENTS 3,615,599  10/1971  Sakamoto et al. ............................ 201/7
5,401,526  3/1995  Tomita ..................................... 426/615

FOREIGN PATENT DOCUMENTS 1233628  10/1986  Japan .............................. A61K 35/78

OTHER PUBLICATIONS

Chem. Abst 98:15745u, 1983.
Chem. Abst. 115:150132b, 1991.

*Primary Examiner*—John W. Rollins
*Attorney, Agent, or Firm*—Birch, Stewart, Kolasch & Birch

[57] ABSTRACT

A method for making garlic taffy wherein powdered garlic is processed by utilizing wheat malt and water to form a liquified product and subsequently saccharified and concentrated to form the garlic taffy. A garlic beverage is produced by adding water, honey or sugar, citric acid and the like to garlic taffy with heating.

9 Claims, No Drawings

METHOD FOR MANUFACTURING A HEALTH FOOD UTILIZING A GARLIC

BACKGROUND AND SUMMARY OF THE INVENTION

The present invention relates to a method for manufacturing a health food utilizing garlic which is made into a garlic taffy, i.e. garlic with a taffy consistency, or a garlic beverage, wherein garlic is the major raw material. Garlic in such a form renders it available for usual use.

From ancient times, garlic has been known as a food having various medicinal advantages with efficacies in such areas as stomach strengthening, digestive benefits, intestine adjusting, perspiration, urination, phlegm loosening, diarrhea treatment, and other restorative features, whereby the habitual use of "Allicin," which is one of the constituents contained in garlic, has the ability to kill harmful bacteria in a manner similar to antibiotics such as Penicillin or Tetramycin. Also, garlic containing Allicin is known to strengthen the immune system and inhibit the onset of cancer thought to be due to the presence of sulfides within the garlic product. In fact, it has already been proven through tests that garlic is a non-toxic natural food which exhibits efficacy as a resistivity and basic body strengthening agent.

The present invention is directed to a method of making a garlic taffy or a garlic beverage wherein garlic is the major raw material thereof.

DETAILED DESCRIPTION OF THE INVENTION

The present invention will be described in more detail hereinbelow in connection with the following examples which are presented as exemplary of the present invention and therefor should not be considered as limiting the scope thereof.

The following Examples 1 to 5 are directed to the manufacture of garlic taffy.

EXAMPLE 1

Raw garlic peeled from a hull is finely cut or crushed and dried at a temperature of about 30°–80° C., preferably 30°–40° C. for 8–12 hours, preferably for 4–5 hours. The drying can be cool air drying, hot temperature drying, or refrigeration and vacuum drying. In a second step, the dried garlic is then made into a powder by use of a grinder. In a third step, an embryo bud of wheat (malt) in an amount of 1–3% by weight is added to 70–75% by weight of powdered garlic and then the mixture is heated at 120°–160° C. whereby it is liquified. In a fourth step, the liquified material thus obtained is conveyed through a fabric filter and then saccharified at 60°–70° C. for 5–7 hours. In a fifth step, the liquid recovered as a result of the saccharification is slowly concentrated whereby a liquid taffy is obtained, which can be further concentrated to form a solid taffy.

EXAMPLE 2

All conditions of example 1 where followed, with the exception of the third step of the process. In the third step at least one starch, for example, glutinous rice, sweet potato, corn, potato, etc. in an amount of 30–40% by weight is mixed with 30–40% by weight of powdered garlic, 20–25% by weight of water and 1–3% by weight of the malt.

EXAMPLE 3

In the first step of the process 30–90% by weight of garlic peeled from the hull is used as is or it is finely cut or crushed, and 10–70% by weight, e.g. rice, sweet potato, corn, potato and 1–3% by weight of malt are added and mixed together. In a second step, water is added to the mixture which is thus liquified at 120°–160° C. The liquified material of the second step is conveyed through a fabric filter and then saccharified for 5–7 hours and then slowly concentrated whereby the liquid taffy thus formed is further concentrated into a solid taffy.

EXAMPLE 4

In a first step, garlic is peeled off the hull and placed into a garlic extruder where garlic juice is squeezed out. In a second step, 10–90% by weight of the garlic juice, 10–90% by weight of starch, and 1–3% by weight of enzyme and malt are added and hydrolyzed into liquid form. In a third step, the liquified material produced by the second step is conveyed through a fabric filter and saccharified for 5–7 hours and then slowly concentrated to form a liquid taffy which is further concentrated into a solid taffy.

The following examples 6 and 7 are directed to the manufacture of garlic beverage.

EXAMPLE 6

Water is added to garlic taffy in an amount of 200 cc water to about 5–10 g of garlic taffy produced hereinabove and then heated, dissolved and diluted. A small amount of honey or sugar is added to produce the desired garlic beverage.

EXAMPLE 7

Water is added to garlic taffy in an amount of 200 cc water to about 5–10 g of garlic taffy produced hereinabove and then heated, dissolved and diluted. A small amount of honey and citric acid, "Puerarin" extracted from Pueraria root juice and "Chungung juice" are further added and the resulting product is sterilized, sealed and packaged.

The sterilization is effected at 87° C. for 30 seconds in order to minimize any loss in benefit of the effective ingredients.

In accordance with the present process, since the garlic smell and the strong garlic action are neutralized during heating at 120°–160° C. to form the garlic taffy, the smell and taste peculiar to garlic are eliminated, and thus it is possible to readily eat or drink the garlic product with no difficulty.

Since tender garlic taffy is made in a state whereby the ingredients of the garlic is maintained as they are without loss of its nutrients, it is possible to improve the health of an old and feeble person or a young child. The garlic beverage can be mixed with an alcoholism eliminating agent, a digestion promoting agent or the like extracted from herb medicine, including honey and citric acid. Thus, the product of the present invention is a health beverage which is good to take as a general beverage which possesses many beneficial properties for the human being including a healthy stomach and an anti-cancer function.

What is claimed is:

1. A method for manufacturing a health food utilizing garlic which comprises mixing a dried, powdered garlic with a malt and water and heating the liquified mixture at 120°–160° C., filtering the liquified mixture and then saccharifying the mixture at a temperature of 60°–70° C. to form a garlic taffy.

2. The method for manufacturing a health food utilizing garlic as defined in claim 1, wherein a garlic taffy is made by adding a starch to the powdered garlic, malt and water mixture.

3. The method for manufacturing a health food utilizing garlic, wherein a garlic beverage is made by adding water to the garlic taffy of claim 1 and heating and dissolving the diluted garlic taffy and adding thereto a small amount of honey or mixture.

4. The method for manufacturing a health food utilizing garlic, wherein a garlic beverage is made by adding water to the garlic taffy of claim 1 and heating, dissolving and diluting the mixture and then adding a small amount of honey and Puerarin, citric acid, and Chungung juice in a predetermined quantity and sealing and packaging the resulting product.

5. The method of claim 1, wherein 20 to 25% water is added to the powdered garlic, starch and malt mixture.

6. The method of claim 1, wherein water is added to the garlic taffy and the mixture is heated followed by the addition of honey or sugar to form a garlic beverage.

7. The method of claim 1, wherein water is added to the garlic taffy and the mixture is heated followed by the addition of honey or sugar, citric acid, Puerarin, and Chungung juice, and sealing and packaging the resultant product.

8. A method for manufacturing garlic taffy which comprises:

drying cut or crushed garlic at a temperature of about 30° to 80° C., converting the dried garlic into a garlic powder, adding wheat malt and water to the garlic powder and heating the mixture at a temperature of 120°–160° C. to form a liquified product, filtering the liquified product, saccharifying the resulting product at a temperature of 60°–70° C., and concentrating the saccharified product to form garlic taffy.

9. The method of claim 8 wherein 10 to 90% by weight starch and 1 to 3% by weight of the malt is added to 10 to 90% by weight of the powdered garlic.

\* \* \* \* \*